United States Patent [19]

Sarantakis

[11] 3,931,140

[45] Jan. 6, 1976

[54] (H-GLY-GLY-TYR-ALA)¹-SOMATOSTATIN

[75] Inventor: Dimitrios Sarantakis, West Chester, Pa.

[73] Assignee: American Home Products Corporation, New York, N.Y.

[22] Filed: Jan. 27, 1975

[21] Appl. No.: 544,434

[52] U.S. Cl............................ 260/112.5 R; 424/177
[51] Int. Cl.².................. C07C 103/52; A61K 37/00
[58] Field of Search............................. 260/112.5 R

[56] References Cited
UNITED STATES PATENTS

| 3,842,066 | 10/1974 | McKinley et al............. 260/112.5 R |
| 3,842,067 | 10/1974 | Sarantakis................... 260/112.5 R |
| 3,882,098 | 5/1975 | Sarantakis................... 260/112.5 R |

Primary Examiner—Lewis Gotts
Assistant Examiner—Reginald J. Suyat
Attorney, Agent, or Firm—Richard K. Jackson

[57] ABSTRACT

The growth hormone release inhibiting compound.

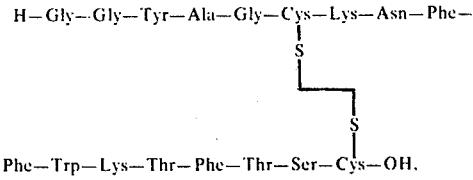

the protamine zinc, protamine aluminum and non-toxic acid addition salts thereof as well as the corresponding linear heptadecapeptide and intermediates therefore are herein described.

5 Claims, No Drawings

(H-GLY-GLY-TYR-ALA)¹-SOMATOSTATIN

BACKGROUND OF THE INVENTION

The structure of the growth hormone release inhibiting factor, somatostatin, has been determined by Brazeau et al., Science, 179, 77(1973). Several techniques for synthesizing somatostatin have been reported in the literature, including the solid phase method of Rivier, J.A.C.S. 96, 2986(1974) and the solution methods of Sarantakis et al., Biochemical Biophysical Research Communications 54, 234(1973) and Immer et al., Helo. Chim. Acta, 57, 730(1974).

DESCRIPTION OF THE INVENTION

In accordance with this invention, there is provided a growth hormone release inhibiting compound of the formula; (H-Gly-Gly-Tyr-Ala)¹-Somatostatin, the non-cyclic form of that heptadecapeptide, the protamine zinc and protamine aluminum adducts and non-toxic acid addition salts thereof as well as the protected intermediates useful for the synthesis of that heptadecapeptide. The heptadecapeptide of this invention is useful in the treatment of conditions characterized by excessive growth hormone production, such as juvenile diabetes and acromegaly.

The heptadecapeptide of this invention (H-Gly-Gly-Try-Ala)¹-Somatostatin presents the amino acid sequence:

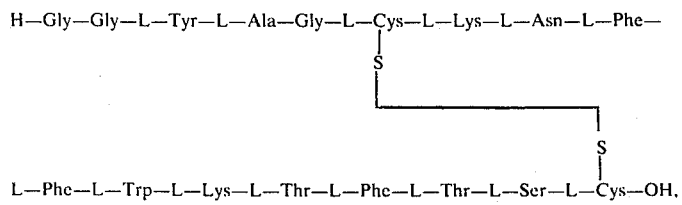

H—Gly—Gly—L—Tyr—L—Ala—Gly—L—Cys—L—Lys—L—Asn—L—Phe—
L—Phe—L—Trp—L—Lys—L—Thr—L—Phe—L—Thr—L—Ser—L—Cys—OH, in its [6–17] cyclic form and is devoid of the disulfide linkage in the linear form. The protamine zinc and protamine aluminum derivatives of the heptadecapeptide represent derivatives conventionally derived from polypeptides for characterization and administrative purposes. The acid addition salts of the heptadecapeptide are derived from both inorganic and organic acids known to afford pharmaceutically acceptable non-toxic addition products, such as hydrochloric, hydrobromic, sulfuric, phosphoric, maleic, acetic, citric, benzoic, succinic, malic, ascorbic acid and the like.

The heptadecapeptide of this invention is prepared by solid phase methodology, employing as the initial reactant the fully protected peptidoresin R-Ala-Gly-Cys (R²)-Lys (R³)-Asn-Phe-Phe-Trp-Lys (R⁴)-Thr(R⁵)-Phe-Thr (R⁶)-Ser (R⁷)-Cys (R⁸)-O-Resin, in which each of the protective R groups are defined, infra. Deprotection of the α-amino protecting group (R) of the alanyl moiety followed by the sequential coupling and deprotection of each of the newly introduced intermediate amino acids tyrosine and glycine followed by the introduction of the terminal glycyl group affords the fully protected intermediate R-Gly-Gly-Tyr(R¹)-Ala-Gly-Cys (R²)-Lys (R³)-Asn-Phe-Phe-Trp-Lys (R⁴)-Thr (R⁵)-Phe-Thr (R⁶)-Ser (R⁷)-Cys (R⁸)-O-Resin, which is totally deprotected and removed from the Resin support by treatment with liquid hydrofluoric acid in the presence of anisole to yield the linear heptadecapeptide H-Gly-Gly-L-Tyr-L-Ala-Gly-L-Cys-L-Lys-L-Asn-L-Phe-L-Phe-L-Trp-L-Lys-L-Thr-L-Phe-L-Thr-L-Ser-L-Cys-OH. If desired, the fully protected heptadecapeptide may be removed from the Resin support by methanolysis to yield the 17-Cysteine methyl ester of the fully protected linear heptadecapeptide. The methylester may then be converted to the free carboxylic acid by mild hydrolysis and the protecting groups may be subsequently removed by treatment with liquid HF in the presence of anisole or by catalytic (e.g. Pd. on BaSO₄) hydrogenation under conditions avoiding attack of the tryptophan moiety.

The deprotected linear heptadecapeptide is readily converted to the [6–17] cyclic disulfide (H-Gly-Gly-Tyr-Ala)¹-Somatostatin by mild oxidation (e.g. air), preferably through exposure of a solution of the linear compound to atmospheric oxygen. The protamine zinc and protamine aluminum complexes and non-toxic acid addition salts are produced by methods conventional in the polypeptide art.

Thus the intermediates which constitute part of this invention may be represented as:

R-Gly-Gly-Tyr (R¹)-Ala-Gly-Cys (R²)-Lys (R³)-Asn-Phe-Phe-Trp-Lys (R⁴)-Thr (R⁵)-Phe-Thr (R⁶)-Ser (R⁷)-Cys (R⁸)-X, in which X represents —OH, —OCH₃ or —O—CH₂ -[polystyrene resin support];

R represents hydrogen or an α-amino protecting group; R¹ is a protecting group for the phenolic hydroxyl group of the tyrosyl moiety selected from the group consisting of benzyl, 2,6-dichlorobenzyl, benzyloxycarbonyl and 2-bromobenzyloxycarbonyl;

R² and R⁸ are protecting groups for the sulfhydryl group of the two cysteinyl moiety independently selected from the group consisting of benzyl; methyl, methoxy or nitro-benzyl; trityl, benzyloxycarbonyl, benzhydryl, tetrahydropyranyl, carboxymethyl, acetamidomethyl, benzoyl, benzylthiomethyl, ethylcarbamyl, thioethyl, p-methoxybenzyloxycarbonyl, and the sulfonate salt;

R³ and R⁴ are members independently selected from the group consisting of hydrogen and a protecting group for the epsilon amino group of the two lysyl moieties selected from benzyloxycarbonyl; halo- or nitro-benzyloxycarbonyl; tosyl, diisopropylmethoxycarbonyl, t-amyloxy-carbonyl and t-butyloxycarbonyl; and R⁵, R⁶ and R⁷ are selected from the group consisting of hydrogen and a protecting group for the hydroxyl group of the threonyl and seryl moieties, independently selected from acetyl, benzoyl, tert-butyl, trityl, benzyl, 2,6-dichlorobenzyl, and benzyloxycarbonyl.

The α-amino protecting group represented by R may be any group known in the art to be useful in the stepwise synthesis of polypeptides. Illustrative of these known groups for protection of an α-amino group are (a) acyl type protective groups such as formyl, trifluoroacetyl, phthalyl, toluenesulfonyl (tosyl), benzenesulfonyl, nitrophenylsulfenyl, tritylsulfenyl, o-nitrophenoxyacetyl, chloroacetyl, acetyl, α-chlorobutyryl, and the like; (b) urethan type protecting groups such as benzyloxycarbonyl and substituted benzyloxycarbonyl (p-chlorobenzyloxycarbonyl, p-nitrobenzyloxycarbonyl, p-bromobenzyloxycarbonyl, p-methoxybenzyloxycarbonyl, tert-butyloxycarbonyl, diisopropylmethoxycarbonyl, isopropyloxycarbonyl, ethoxycarbonyl, allyloxycarbonyl, cyclopentyloxycarbonyl, adamantyloxycarbonyl, cyclohexyloxycarbonyl, phenylthiocarbonyl, and the like; (c) aralkyl type protecting groups as illustrated by triphenylmethyl, benzyl, and the like; and (d) trialkylsilane groups such as trimethylsilane. The preferred α-amino protecting group defined by R is tert-butyloxycarbonyl.

The criterion for selecting protecting groups for $R^{1-8}$ are (a) the protecting group must be stable to the reagent and under the reaction conditions selected for removing the α-amino protecting group at each step of the synthesis, (b) the protecting group must retain its protecting properties (i.e., not be split off under coupling conditions), and (c) the side chain protecting group must be removable upon the completion of the synthesis of the desired amino acid sequence, under reaction conditions that will not alter the peptide chain.

The group —O—CH$_2$—[polystyrene resin support] defining X in the intermediates of this invention described supra, represents the ester moiety of one of the many functional groups of the polystyrene resin support.

The solid phase method of preparing the heptadecapeptide of this invention is generally known in the art and is described by Merrifield, J.A.C.S., 85, 2149(1963). The resin support employed may be any suitable resin conventionally employed in the art for the solid phase preparation of polypeptides, preferably polystyrene which has been cross-linked with from 0.5 to about 3 percent divinyl benzene, which has been either chloromethylated or hydroxymethylated to provide sites for ester formation with the initially introduced α-amino protected amino acid.

An example of a hydroxymethyl resin is described by Bodanszky et al., Chem. Ind. (London) 38, 1597-98 (1966). A chloromethylated resin is commercially available from Bio Rad Laboratories Richmand, California and the preparation of such a resin is described by Stewart et al., "Solid Phase Peptide Synthesis" (Freeman & Co., San Francisco 1969), Chapter 1, pp 1-6. The α-amino and sulfhydryl protected cysteine is coupled to the chloromethylated resin according to the procedure of Gisin, Helv. Chim. Acta., 56, 1476 (1973). Following the coupling of the α-amino and sulfhydryl protected cysteine to the resin support, the α-amino protecting group is removed by standard methods employing trifluoroacetic acid in methylene chloride, trifluoroacetic acid alone or HCl in dioxane. The deprotection is carried out at a temperature between about 0°C. and room temperature. After removal of the α-amino protecting group the remaining α-amino protected amino acids are coupled, seriatim, in the desired order to obtain the product. Alternatively, multiple amino acid groups may be coupled by the solution method prior to coupling with the resin supported amino acid sequence. The selection of an appropriate coupling reagent is within the skill of the art. A particularly suitable coupling reagent is $N,N^1$-diisopropyl carbodiimide. Other applicable coupling agents are (1) carbodiimides (e.g. $N,N^1$-dicyclohexycarbodiimide, N-ethyl $N^1$-(α-dimethylamino propyl carbodiimide); (2) cyanamides (e.g. N,N-dibenzylcyanamide; (3) ketenimines; (4) isoxazolium salts (e.g. n-ethyl-5-phenyl isoxazolium-3'-sulfonate; (5) monocyclic nitrogen containing heterocyclic amides of aromatic character containing one through four nitrogens in the ring such as imidazolides, pyrazolides, 1,2,4-triazolides, Specific heterocyclic amides that are useful include N,N'-carbonyl diimidazole, N,N'-carbonyl-di-1,2,4-triazole; (6) alkoxylated acetylene (e.g. ethoxyacetylene); (7) reagents which form a mixed anhydride with the carboxyl moiety of the amino acid (e.g. ethylchloroformate, isobutylchloroformate) and (8) nitrogen containing heterocyclic compounds having a hydroxy group on one ring nitrogen (e.g. N-hydroxyphthalimide, N-hydroxysuccinimide, 1-hydroxybenzotriazole). Other activating reagents and their use in peptide coupling are described by Schroder & Lubke supra, in Chapter III and by Kapoor, J. Pharm. Sci., 59, pp. 1-27, (1970).

Each protected amino acid or amino acid sequence is introduced into the solid phase reactor in about a fourfold excess and the coupling is carried out in a medium of dimethylformamide: methylene chloride (1:1) or in dimethylformamide or methylene chloride alone. In cases where incomplete coupling occurred the coupling procedure is repeated before removal of the α-amino protecting group, prior to introduction of the next amino acid to the solid phase reactor. The success of the coupling reaction at each stage of the synthesis is monitored by the ninhydrin reaction as described by E. Kaiser et al., Analyt. Biochem, 34, 595 (1970).

The in vivo activity of the heptadecapeptide of this invention was established by injecting Nembutal intraperitoneally into rats weighing between 200 to 250 grams in an amount of 50 milligrams per kilogram body weight. After five minutes, the heptadecapeptide of this invention was administered to the rats in a dose of 500 micrograms per kilogram body weight from a solution made from three milligrams of the heptadecapeptide, 1.2 milliliters of water and 4.8 milliliters of polyethylene glycol (PEG 400). The rats blood was sampled 15 minutes after administration of the heptadecapeptide and the amount of growth hormone present in the plasma was determined by radioimmunoassay. In one determination, with eight control rats presenting an average of 86 ± 15 nanograms growth hormone per milliliter of plasma, the eight treated animals had an average of 9 ± 4 nanograms growth hormone per milliliter of plasma ($p<0.01$). In another experiment employing twelve rats for control and testing, the control group had an average of 66 ± 10 nanograms growth hormone per milliliter of plasma while the treated animals had 21 ± 7 nanograms growth hormone per milliliter of plasma ($p<0.01$).

The heptadecapeptide is the first discovered polypeptide containing more amino acid residues than somatostatin itself, to exhibit inhibition of growth hormone secretion or to reduce growth hormone concentration in blood plasma. In fact, the activity of the compound of this invention exceeds the activity of somatostatin in reducing growth hormone concentrations in blood plasma. Therefore, the heptadecapeptide of this invention is useful in the prevention of excessive secretion of somatotropin in domestic animals and for the control of the immuno-reactive pituitary growth hormone in comparative and experimental pharmacology. From the known relationship between growth hormone control in standard experimental animal and the human, the activity of the disclosed heptadecapeptide characterizes the compound as useful in the treatment of acromegaly and juvenile diabetes in the same manner as somatostatin itself. Administration of the heptadecapeptide may be by conventional routes common to somatostatin and related polypeptides, under the guidance of a physician, orally or parenterally, in an amount dictated by the extent of the dysfunction as determined by the physician. The compound may be administered alone or in conjunction with conventional pharmaceutically acceptable carriers and adjuvants, in unit dosage form containing from about 2 to about 100 milligrams per kilogram host body weight. Furthermore, the protamine zinc or protamine aluminum adducts present desireable administrable forms of the heptadecapeptide as is conventional in therapy involving the use of polypeptides.

In the following preparatory scheme, the abbreviations employed are:
Boc = tertiary butyloxycarbonyl
MBzl = p-methoxybenzyl
ClZ = 2-chlorobenzyloxycarbonyl
Bzl = benzyl
$CH_2Bzl$ = 2,6-dichlorobenzyl

EXAMPLE 1 tert-Butyloxycarbonyl-glycyl-glycyl-O-2,6-dichlorobenzyl-L-tyrosyl-L-alanyl-glycyl-S-p-methoxybenzyl-L-cysteinyl-N$^\epsilon$-2-chlorobenzyloxycarbonyl-L-lysyl-L-asparaginyl-L-phenylalanyl-L-phenylalanyl-L-tryptophyl-N$^\epsilon$-2-chlorobenzyloxycarbonyl-L-lysyl-O-benzyl-L-threonyl-L-phenylalanyl-O-benzyl-L-threonyl-O-benzyl-L-seryl-S-p-methoxybenzyl-L-cysteinyl-hydroxy methyl polystyrene.

The peptidoresin Boc-Ala-Gly-Cys (SMBzl)-Lys (ClZ)-Asn-Phe-Phe-Trp-Lys (ClZ)-Thr (Bzl)-Phe-Thr (Bzl)-Ser (Bzl)-Cys (SMBzl)-O-methylpolystyrene was prepared by conventional solid phase techniques reported in the literature. Deprotection of the α-amino group of alanine was effected by treatment with trifluoroacetic acid - $CH_2Cl_2$ - 1,4-dithioerythritol (1:1:0.5 percent) for thirty minutes at room temperature in a Merrifield solid phase reaction flask. The product was washed with $CH_2Cl_2$ (3 times), dimethylformamide, dimethylformamide-triethylamine (12 percent), $CH_2Cl_2$-triethylamine (12 percent) and $CH_2CL_2$ (3 times). A positive ninhydrin test was obtained after the method of Kaiser et al., Anal. Biochem, 34, 595(1970). The peptido resin was then treated with Boc-Tyr ($Cl_2Bzl$)-OH (7 grams) in dimethylformamide-$CH_2Cl_2$(2:1) followed by disopropylcarbodiimide (4 milliliters) in two portions in $CH_2Cl_2$. The mixture was shaken overnight, filtered and the treatment repeated with one half the original amount of Boc-Tyr ($Cl_2Bzl$)-OH and diisopropylcarbodiimide. The mixture was filtered and washed with $CH_2Cl_2$ (two times), dimethylformamide (three times) and $CH_2Cl_2$ (three times). The ninhydrin test on the product was negative. The peptidoresin was then deprotected following the preceding method and treated with Boc-Gly-OH (2.8 grams) and diisopropylcarbodiimide (4 milliliters) overnight. This treatment was again repeated with half the quantity of materials and the complete cycle repeated for the incorporation of the second Boc-Gly-OH to afford a 4.3 gram yield of the title peptidoresin.

EXAMPLE 2

Glycyl-glycyl-L-tyrosyl-L-alanyl-glycyl-L-cysteinyl-L-lysyl-L-asparaginyl-L-phenylalanyl-L-phenylalanyl-L-tryptophyl-L-lysyl-L-threonyl-L-phenylalanyl-L-threonyl-L-seryl-L-cysteine[6–17 cyclic disulfide]

The peptidoresin of Example 1 (4.7 gr.) was mixed with 5 ml. anisole and treated with 100 ml. liquid HF in vacuo. The mixture was stirred for 45 minutes at room temperature, then the excess HF was removed in vacuo as fast as possible (ca. 90 minutes time). The residue, the linear form of the title compound, was washed with dry diethyl ether by decantation under a $N_2$ atmosphere and then extracted with 1 percent aqueous acetic acid which was flushed with $N_2$. The aqueous solution was diluted to 1500 ml. and brought to pH ≈ 8 with dilute $NH_4OH$, stirred for 24 hours with exposure to atmospheric oxygen and lyophilized to yield, 1.3 gram of the cyclic disulfide as a white solid. This crude product was chromatographed through a column of Sephadex G-25 which was equilibrated first with the lower phase of a mixture of n-butanol-acetic acid — water (4:1:5) then with the upper phase and eluted with the upper phase. The fractions (7 ml. each) which emerged in the 55–77 tubes were pooled and lyophilized to yield 86 mg. of a fluffy white solid. $R_f$ (n-butanol-water-acetic acid, 4:5:1 upper phase)0.41 $R_f$ (i-amyl alcohol-water-pyridine, 7:6:7) 0.52. Aminoacid analysis, Asp (1) 0.99, Thr(2) 2.08, Ser (1) 0.88, Gly (3) 3.1, Ala(1) 1, Tyr(1) 0.93, Phe (3) 3.16, Lys(2) 2.16, $NH_3$ (1) 1.62, Trp and Cys N.D.

What is claimed is:
1. A compound selected from the group consisting of

H-Gly-Gly-L-Tyr-L-Ala-Gly-L-Cys-L-Lys-L-Asn-
                           |
                           S
                           |
                           |
                           |
                           S
                           |
L-Phe-L-Phe-L-Trp-L-Lys-L-Thr-L-Phe-L-Thr-L-Ser-L-Cys-OH, the corresponding linear heptadecapeptide, the protamine zinc, protamine aluminum and non-toxic acid addition salts thereof.

2. The heptadecapeptide of claim 1 which is glycyl-glycyl-L-tyrosyl-L-alanylglycyl-L-cysteinyl-L-lysyl-L-asparaginyl-L-phenylalanyl-L-phenylalanyl-L-tryptophyl-L-lysyl-L-threonyl-L-phenylalanyl-L-threonyl-L-seryl-L-cysteine.

3. The heptadecapeptide of claim 1 which is glycyl-glycyl-L-tyrosyl-L-alanylglycyl-L-cysteinyl-L-lysyl-L-asparaginyl-L-phenylalanyl-L-phenylalanyl-L-tryptophyl-L-lysyl-L-threonyl-L-phenylalanyl-L-threonyl-L-seryl-L-cysteine [6–17 disulfide].

4. A heptadecapeptide of the formula R-Gly-Gly-Try($R^1$)-Ala-Gly-Cys($R^2$)-Lys($R^3$)-Asn-Phe-Phe-Trp-Lys($R^4$)-Thr ($R^5$)-Phe-Thr ($R^6$)-Ser ($R^7$)-Cys ($R^8$)-O-X in which R is a member selected from the group consisting of hydrogen and an α-amino protecting group; $R^1$ is a protecting group for the phenolic hydroxyl group of the tyrosyl moiety selected from the group consisting of benzyl, 2,6-dichlorobenzyl, benzyloxycarbonyl and 2-bromobenzyloxycarbonyl;

$R^2$ and $R^8$ are protecting groups for the sulfhydryl group of the two cysteinyl moiety independently selected from the group consisting of benzyl; methyl, methoxy or nitro-benzyl; trityl, benzyloxycarbonyl, benzhydryl, tetrahydropyranyl, carboxymethyl acetamidomethyl, benzoyl, benzylthiomethyl, ethylcarbamyl, thioethyl, p-methoxybenzyloxycarbonyl, and the sulfonate salt;

$R^3$ and $R^4$ are members independently selected from the group consisting of hydrogen and a protecting group for the epsilon amino group of the two lysyl moieties selected from benzyloxycarbonyl; halo- or nitro-benzyloxycarbonyl; tosyl, diisopropylmethoxycarbonyl, t-amyloxy-carbonyl and t-butyloxycarbonyl;

$R^5$, $R^6$ and $R^7$ are selected from the group consisting of hydrogen and a protecting group for the hydroxyl group of the threonyl and seryl moieties, independently selected from acetyl, benzoyl, tert-butyl, trityl, benzyl, 2,6-dichlorobenzyl, and benzyloxycarbonyl;

and

X is a member selected from the group consisting of hydroxy, methoxy and $-O-CH_2-$[polystyrene resin support], wherein said polystyrene resin is cross linked with from 0.5 to about 3 percent divinylbenzene.

5. The compound of claim 4 in which R is t-butyloxycarbonyl, $R^1$ is 2,6-dichlorobenzyl, $R^2$ and $R^8$ are p-methoxybenzyl, $R^3$ and $R^4$ are 2-chlorobenzyloxycarbonyl and $R^5$ and $R^6$ and $R^7$ are benzyl.

* * * * *

UNITED STATES PATENT OFFICE
CERTIFICATE OF CORRECTION

PATENT NO. : 3,931,140
DATED : January 6, 1976
INVENTOR(S) : Dimitrios Sarantakis It is certified that error appears in the above-identified patent and that said Letters Patent are hereby corrected as shown below:

Column 6, line 59, delete Try and insert Tyr.

Signed and Sealed this fourth Day of May 1976

[SEAL]

Attest:

RUTH C. MASON
Attesting Officer

C. MARSHALL DANN
Commissioner of Patents and Trademarks